United States Patent
Kowalczyk et al.

(10) Patent No.: US 6,406,450 B1
(45) Date of Patent: Jun. 18, 2002

(54) ORTHOPEDIC ANKLE BRACE

(75) Inventors: Gregory Kowalczyk, Hoboken; Fabian McCarthy, Basking Ridge; Henry J. McVicker, Madison; Mario A. Turchi, Tenafly; Eric Watts; Scott Salmon, both of Hoboken, all of NJ (US)

(73) Assignee: Aircast, Inc., Summit, NJ (US)

( * ) Notice: Subject to any disclaimer, the term of this patent is extended or adjusted under 35 U.S.C. 154(b) by 0 days.

(21) Appl. No.: 09/490,479

(22) Filed: Jan. 24, 2000

(51) Int. Cl.[7] .............................. A61F 5/00; A61F 13/00
(52) U.S. Cl. ............................ 602/27; 602/65; 128/882
(58) Field of Search .................................. 602/5, 14, 23, 602/27, 60–62, 65; 128/882; 36/140, 2 R, 106, 114; 2/22

(56) References Cited

U.S. PATENT DOCUMENTS

| | | | |
|---|---|---|---|
| 3,674,023 A | | 7/1972 | Mann |
| 4,280,489 A | | 7/1981 | Johnson, Jr. |
| 4,414,965 A | * | 11/1983 | Mauldin et al. ............... 128/87 |
| 4,497,070 A | * | 2/1985 | Cho ................. 2/22 |
| 4,624,015 A | * | 11/1986 | Bottoms ........................ 2/22 |
| 4,638,794 A | * | 1/1987 | Grisar ...................... 128/80 H |
| 4,756,026 A | * | 7/1988 | Piece, Jr. ........................ 2/16 |
| 5,014,691 A | * | 5/1991 | Cueman et al. ............... 128/80 |
| 5,125,400 A | | 6/1992 | Johnson, Jr. |
| 5,209,722 A | | 5/1993 | Miklaus et al. |
| 5,217,431 A | | 6/1993 | Toronto et al. |
| 5,330,419 A | | 7/1994 | Toronto et al. |
| 5,366,439 A | | 11/1994 | Peters |
| 5,445,602 A | * | 8/1995 | Grim et al. .................... 602/27 |
| 5,507,720 A | * | 4/1996 | Lampropoulos .............. 602/27 |
| 5,697,893 A | | 12/1997 | Rhenter |
| 5,713,837 A | | 2/1998 | Grim et al. |
| 5,741,222 A | * | 4/1998 | Fiore ............................ 602/27 |
| 5,897,520 A | | 4/1999 | Gerig |

\* cited by examiner

*Primary Examiner*—Denise M. Pothier
(74) *Attorney, Agent, or Firm*—Jones, Day Reavis & Pogue (57) ABSTRACT

A unitary boot-type ankle brace is provided having the capability of stabilizing an ankle against inversion and eversion without limiting normal plantarflexion and dorsiflexion of the ankle and while simultaneously providing focal compression of the anterior talofibular ligament. The brace is preferably constructed of a flexible material and includes a medial side portion dimensioned and configured to extend along a medial side of a user's leg and foot, and having a lateral side portion dimensioned and configured to extend along a lateral side of the leg and foot. The side portions are joined to a forwardly extending forefoot sleeve portion and to a base portion. In a primary aspect of the invention the side portions define a rear opening for insertion of the foot with a strap for selectively connecting the side portions adjacent the user's heel.

5 Claims, 7 Drawing Sheets

ORTHOPEDIC ANKLE BRACE

BACKGROUND OF THE INVENTION

1. Field of the Invention

The present invention relates generally to orthopedic devices and more particularly to ankle braces for stabilizing the ankle against inversion and eversion without limiting normal plantarflexion and dorsiflexion of the ankle and which can be easily fitted to an ankle and worn with a conventional shoe.

2. Description of the Related Art

In the management of certain injuries to the lower extremities such as fractures of the tibia and fibula, malleolar fractures, or severe ankle sprains, it is common to completely immobilize the lower extremity by use of the well-known molded plaster or resin cast.

Once the injured extremity has become stable, however, it has been found that recovery may be effected more rapidly by gradually and progressively permitting the extremity to bear weight and undergo other permitted exercises. Thus, for example, an orthopedic brace such as those disclosed in U.S. Pat. Nos. 4,280,489 and 5,125,400, both of which are assigned to the assignee herein and incorporated herein by reference in their entirety, may be utilized. These braces are pneumatic braces featuring one or more rigid outer shell members having associated therewith an inflatable liner or air cell for engaging a body part or limb. Commercial embodiments of the pneumatic brace incorporating the inventions disclosed in these prior patents are adapted to be fixed about the lower leg and typically comprise an outer shell member, or sidewall, in the form of a U-shaped stirrup having inflatable liners or air cells disposed within the stirrup member in co-extensive relation to the upstanding sidewalls thereof. Strap fastening means maintain the member sidewalls in engagement with confronting portions of the lower leg whereby each air cell serves as a firm supporting cushion of pressurized air between the irregular contours of the lower leg and the member sidewalls.

This brace construction is capable of stabilizing the ankle against eversion and inversion while permitting dorsiflexion and plantarflexion and while being worn inside a conventional shoe. Thus ambulatory functionality and permitted exercises are feasible thereby encouraging more rapid recovery from various injuries to the lower extremity, such as ankle sprains, than otherwise would be possible. The braces are used for ankle sprain management in many countries because of their effectiveness, comfort and convenience in mobilizing yet protecting the ankle from re-injury. They have made "functional management" practicable.

The most common ankle injury is a sprain of the anterior talofibular ligament (ATFL) at the anterior margin of the lateral malleolus where swelling and edema originates. Since the ATFL is in the anterior front portion of the ankle, it lies in the uncovered area between the two sides of the stirrup member. To compensate for this uncovered area, many practitioners use a supplemental compression wrap during the initial few days after injury. An elastic ankle wrap is used just for this purpose.

Thus the recovery rate for ankle function following an inversion sprain may be related to the effectiveness of edema control at the injury site. Numerous authors have reported the use of a U-shaped felt or foam rubber device beneath an elastic wrap or adhesive tape for applying focal compression to the soft tissues adjacent to the fibular malleolus. See, for example, Wilkerson et al., "Treatment of the Inversion Ankle Sprain: Comparison of Different Modes of Compression and Cryo Therapy", JOSPT, Volume 17, No. 5, May 1993, pages 240–246. Focal compression consists of pressure application to surface concavities while adjacent proximal convex bony prominences are left uncompressed. See Wilkerson, "Treatment of the Inversion Ankle Sprain through Synchronous Application of Focal Compression and Cold", ATHLETIC TRAINING, JNATA, Volume 26, Fall 1991, pages 220–237. One of the objectives of the studies, as set forth in these articles, was to add focal compression to the uncovered area between the two sides of the stirrup with a pathway up the center of the stirrup for drainage of edema from the area of high pressure to the area of low pressure.

One form of ankle brace that has proved to be particularly effective for control of edema and swelling following a severe sprain is disclosed in U.S. Pat. No. 5,389,065 which is assigned to the assignee herein, the disclosure of which is incorporated by reference in its entirety. Shown and described in the '065 patent is a stirrup-type ankle brace having an outer shell member, the shell member having a lateral elongated, substantially rigid, support member with a corresponding supporting cushion thereon substantially coextensive therewith and an opposed medial support member with a corresponding cushion thereon. The lateral supporting cushion has a pre-inflated flap extending along the anterior margin of its distal end with enough width to cover the area over and surrounding the anterior talofibular ligament. The flap is compressed against the ATF ligament by a strap of elastic hook-and-loop compatible material. A tab of hook material is attached to the anterior end of the elastic strip so that it can engage the opposite end at any length. The strap is retained between the lateral shell and supporting cushion in the preferred embodiment so as to overlap the flap and compress the ATF ligament and medial malleolus when wrapped around the ankle. It does not wrap around either of the shells, but is at the outside surface of the lateral supporting cushion and the inside surface of the medial supporting cushion in the preferred embodiment.

Another form of ankle brace, as disclosed for example in U.S. Pat. Nos. 5,217,431 and 5,330,419, is a boot-type brace. Such braces can effectively be used not only in the rehabilitation phase immediately following the ankle injury, but also during the return to activity phase of the injury, and particularly for use in sports. This brace also has utility as a prophylaxis for healthy ankle joints to prevent new injuries or the recurrence of old injuries during activity. Basically these patents teach a pliant boot that surrounds the ankle joint, as well as the foot and lower leg in the region thereof. The boot may incorporate means of applying compression to the ankle joint. Attached to the boot are a pair of adjustable tension straps vertically disposed about the ankle joint for restricting the mobility thereof. Integral with the boot is a pair of stiffening members positioned about the ankle joint to cooperate with the tension straps in the performance of their mobility restricting function. Further, provided integral with the boot are retention members that isolate the malleoli from the stiffening members for the comfort of the wearer. Finally, one or more retention straps are provided to maintain the stability of the brace.

Other forms of boot-type sport ankle braces are available such as the brace sold under the trade name SPEED BRACE by Royce Medical Company of Camarillo, Calif. and the brace sold under the trade name ASO by Medical Specialties, Inc. of Charlotte, N.C.

A disadvantage of commercially available boot-type ankle braces is that they often inhibit normal plantarflexion and dorsiflexion when worn with conventional shoes, such as athletic shoes, during the activity phase of rehabilitation. Another disadvantage of common boot-type sport ankle braces is that they are typically of top entry construction and have front laces for securely fitting the brace to the foot. These front lacing boots can thus be inconvenient to fit to the ankle and their laces can easily become tangled with the laces of the associated athletic shoe making it difficult for them to be removed when desired.

SUMMARY OF THE INVENTION

The present invention improves over the prior art by providing a unitary boot-type ankle brace having the capability of stabilizing an ankle against inversion and eversion without limiting normal plantarflexion and dorsiflexion of the ankle and while simultaneously providing focal compression of the anterior talofibular ligament. The brace is preferably constructed of a flexible material and includes a medial side portion dimensioned and configured to extend along a medial side of a user's leg and foot, and a lateral side portion dimensioned and configured to extend along a lateral side of the leg and foot. The side portions are joined to a forwardly extending forefoot sleeve portion and to a base portion. In one aspect of the invention the side portions define a rear opening for insertion of the foot, with a strap for selectively connecting the side portions adjacent the user's heel.

In another aspect of the invention the brace includes a strap dimensioned and configured to extend from a lateral portion of the boot and wrap around a front portion of the boot to a medial side of the boot, the strap passing in close proximity to the anterior talofibular ligament of the user when the boot is applied. The strap thus serves not only as a surrogate anterior talofibular ligament, it also serves to provide focal compression to the ligament to thus promote healing.

In yet another aspect of the invention, both the lateral and medial side portions of the boot are preferably formed with pockets, each containing a relatively rigid shell for limiting inversion and eversion of the ankle. In one preferred form the shells are provided with air cells for conforming them comfortably to the shape of the user's lower leg and foot.

BRIEF DESCRIPTION OF THE DRAWINGS

The foregoing and other novel features and advantages of the invention will be appreciated upon a review of the following detailed description taken in conjunction with the accompanying drawings wherein.

DETAILED DESCRIPTION OF THE PREFERRED EMBODIMENTS

Figure 1:
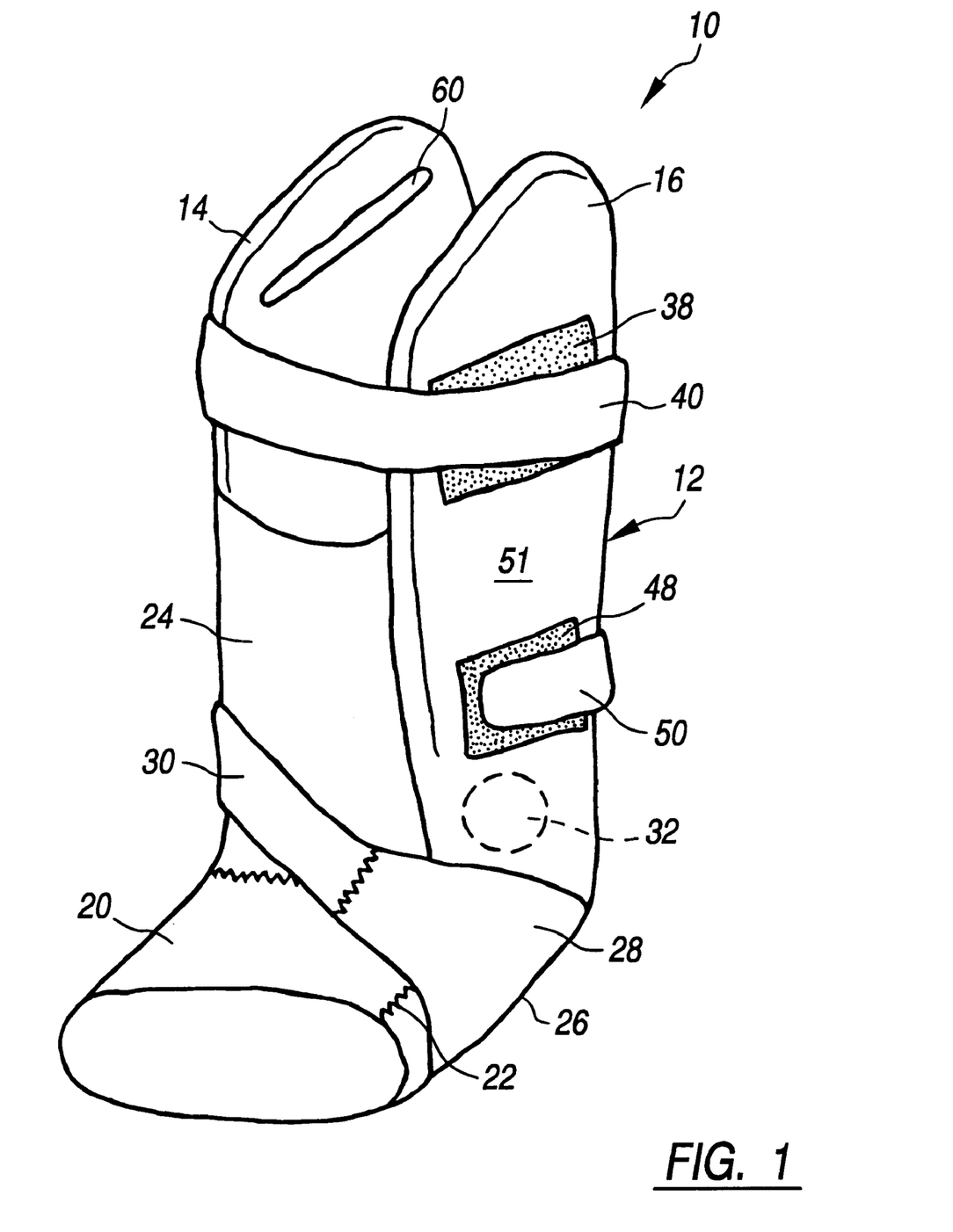
FIG. 1 is a lateral perspective view of an ankle brace constructed in accordance with the principles of the invention and suitable to be applied to the left foot of a user.

Referring now to the drawings, and initially to FIG. 1, a left ankle brace constructed according to the invention is shown in perspective and designated generally by the reference numeral 10. It is understood that while a left ankle brace will be described, the brace 10 can readily be adapted to a right ankle brace by simply reversing its component parts in a manner within the ordinary skill in the art. The ankle brace 10 is generally constructed to be fitted about the lower extremity of a human limb. The term "lower, extremity" as used herein should be interpreted broadly to include the foot, ankle and the lower leg.

Figure 3:
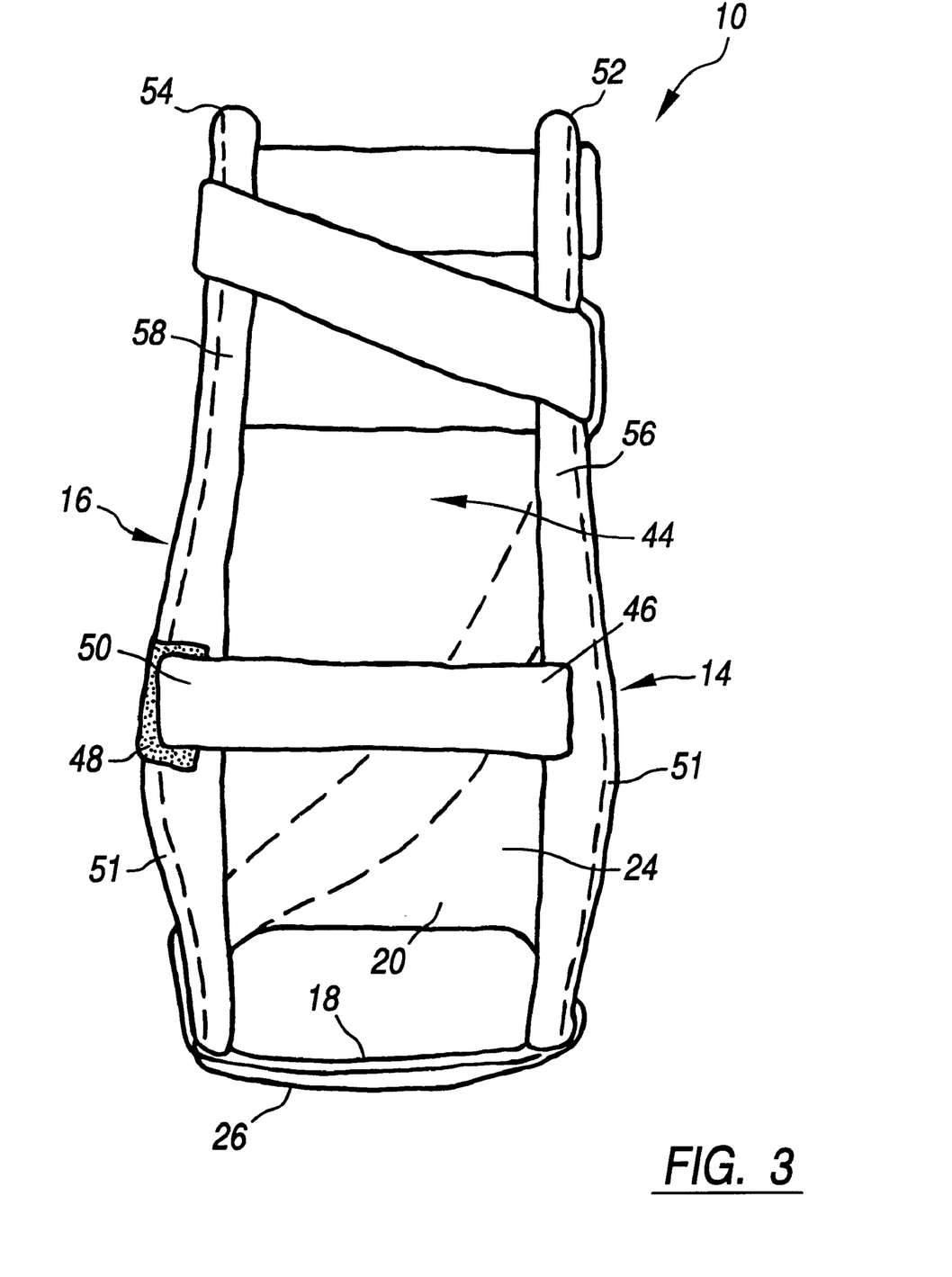
FIG. 3 is a rear view of the brace.
Figure 4:
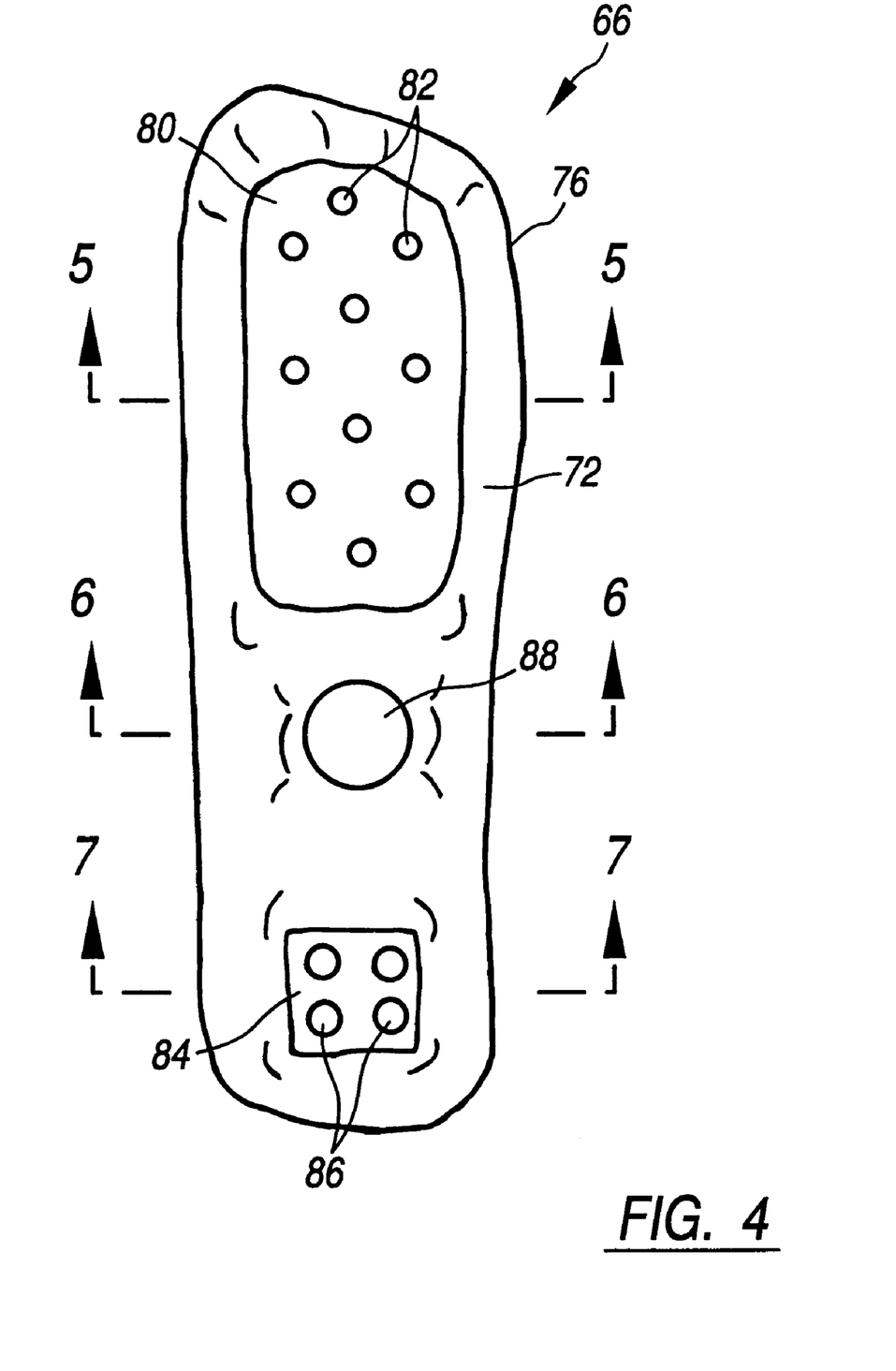
FIG. 4 is a plan view of the interior facing side of a shell member for the lateral side portion of the brace.
Figure 5:
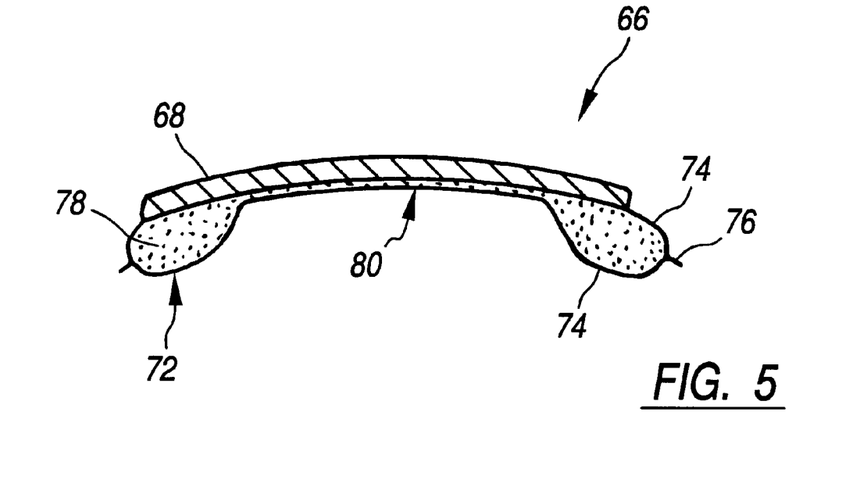
FIG. 5 is an enlarged cross-sectional view taken substantially along the line 5—5 of FIG. 4.

Ankle brace 10 is preferably constructed in the form of a boot 12 made of pliant material such as a laminate of elasticized nylon fabric and neoprene. The boot 12 which may be cut from a flat piece of material, as will be hereinafter described, comprises a generally elongate medial side portion 14 and a complementary generally parallel lateral side portion 16. The side portions 14 and 16 are preferably formed integrally with a base portion 18 dimensioned and configured to pass beneath the heel and a portion of the plantar vault of the user as best seen in FIG. 3. Formed integrally with the side portions 14 and 16 and base portion 18 is a forwardly extending forefoot sleeve 20 which may be closed by a sewn seam 22. A Lycra shin wrap 24 may be attached as by sewing to the front of the side portions 14 and 16 and sleeve 20.

Figure 2:
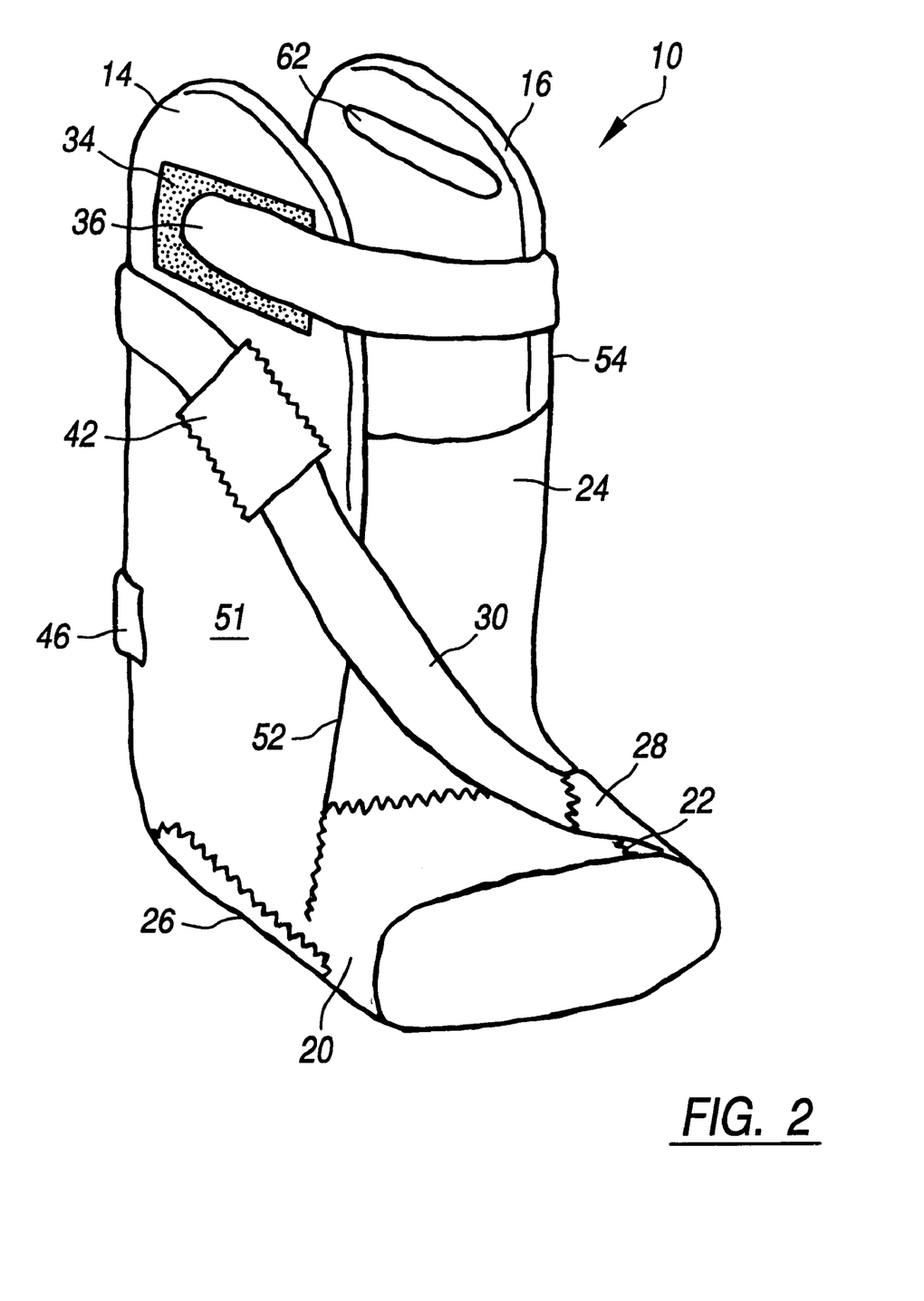
FIG. 2 is a medial perspective view of the brace of FIG. 1.

In accordance with the invention, and as seen in FIGS. 1 and 2, a heel lock strap 26 is attached as by sewing to a lower end of the medial side portion 14 and extends underneath the base portion 18 to the lateral side of the boot 12 where it is configured with a generally triangular-shaped portion 28 and joins an elongate strap 30. The heel lock strap 26 is preferably formed from an inelastic polyester material and the strap 30 from web nylon. The shape of the portion 28 is selected such that the heel lock strap 26 passes adjacent the region 32 of the anterior talofibular ligament when the brace 10 is applied. The strap 30 is of sufficient length that it can be pulled taut across the shin and up and around the upper proximal portions of the side portions 14 and 16 whereupon it can be secured to the medial side portion 14 by fastening means such as may be provided by hook material 34 and complementary loop material 36 of a type sold under the trade name VELCRO. Hook and loop material, 38 and 40, respectively, may also be used on the upper lateral side portion 16 to properly align the strap 30. Thus, the strap 30 serves to positively secure the brace 10 to the lower extremity of the user. To facilitate proper alignment of the strap 30 a sleeve 42 may be provided on the medial side portion 14 through which the strap 30 passes (FIG. 2).

As best seen in FIG. 3, and further in accordance with the invention, the side portions 14 and 16 of the brace 10 are specifically designed to define a rear opening 44. A suitable strap 46 is provided at a height slightly above the heel at the location of the Achilles tendon to position the brace 10 and prevent its shifting anteriorly when applied. Hook material 48 and complementary loop material 50 may be provided for convenience of tightening the strap 46. The strap 46 may be formed from web nylon, for example, or from nylon elastic loop for additional comfort.

Figure 6:
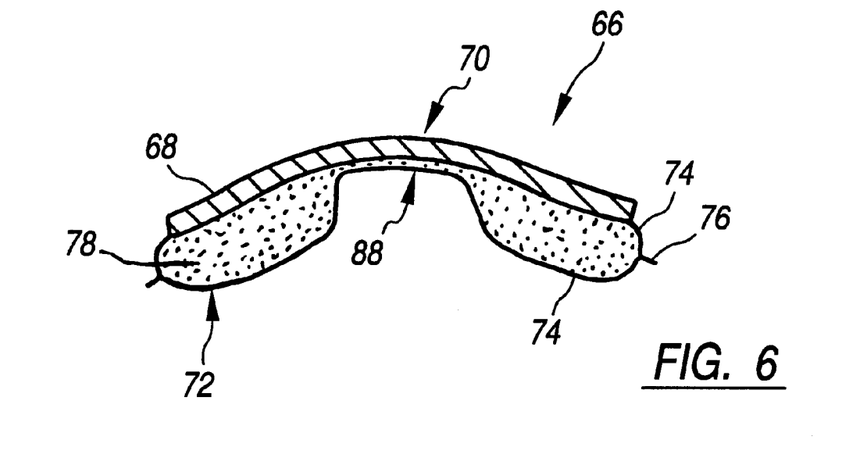
FIG. 6 is an enlarged cross-sectional view taken substantially along the line 6—6 of FIG. 4.
Figure 7:
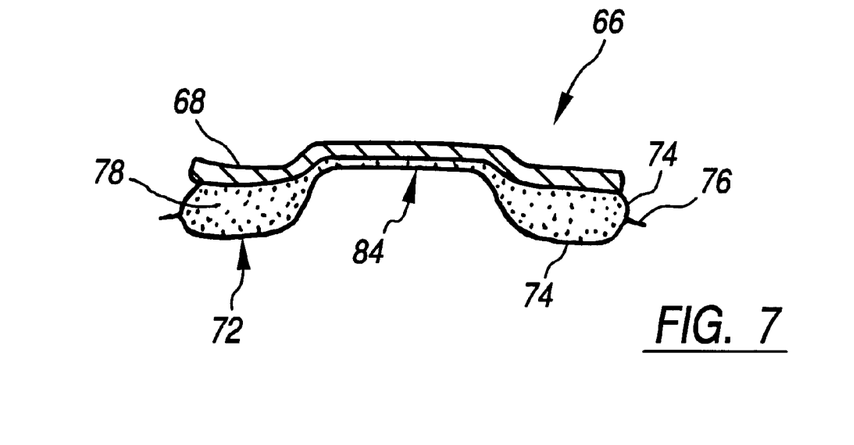
FIG. 7 is an enlarged cross-sectional view taken substantially along the line 7—7 of FIG. 4.

Both the medial and lateral side portions 14 and 16 are each preferably provided with an outer layer 51 of a pliant polyester vinyl material sewn around edges 52 and 54 of the side portions 14 and 16, respectively, to thereby define closed pockets 56 and 58. Slots 60 and 62 may be provided to gain access to the pockets 56 and 58 (FIGS. 1 and 2). The slots are each dimensioned to slidingly receive a shell assembly 66 shown in FIGS. 4–7, only the lateral shell assembly being shown, the medial shell assembly being a mirror image thereof. Each shell assembly 66 comprises a relatively rigid shell 68 which is preferably injection molded from a suitable thermoplastic material such as polypropylene. The shells 68 are contoured to the typical anatomical shape of the lower extremity including having a pronounced indentation 70 for comfortably fitting and receiving the malleoli (see FIG. 6). Secured to each shell 68, as by a suitable adhesive, is an air cell 72 comprising two layers 74 of PVC or urethane heat sealed around their edges 76 and enclosing an open-cell foam material 78. Thus, the air cells 72 are constructed to be preinflated and designed to afford a comfort layer between the lower extremity and shells 68. The air cells 72 are configured to provide a relatively large proximal indentation 80 provided with vent holes 82 formed through the shell 68 and with a distal indentation 84 also formed with vent holes 86. Calcaneus indentations 88 may also be provided to lock in the ankle. The calcaneus indentations 88 are preferably asymmetrically positioned for proper anatomical function.

Figure 8:
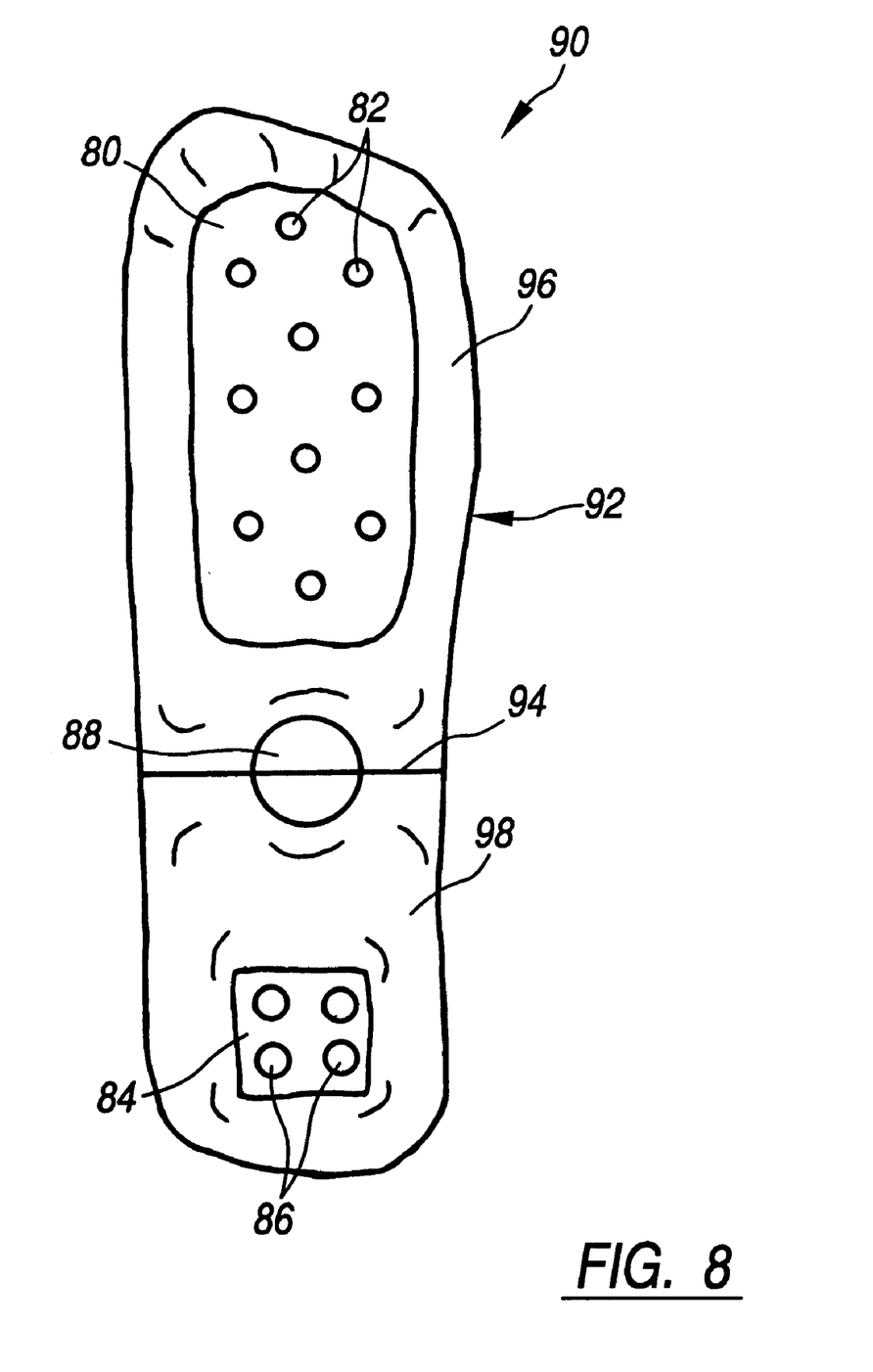
FIG. 8 is a plan view of an alternative shell member for the lateral side portion of the brace.

Referring to FIG. 8, an alternative shell assembly is designated by the reference numeral 90. In this assembly 90 an air cell 92 is provided with a bar seal 94 essentially separating the cell 92 into a proximal chamber 96 and a distal chamber 98. The purpose of such construction is to prevent migration of air from the proximal portion of the air cell to the distal portion of the cell in order to not only reduce the bulk but to minimize the possibility of the extremity bottoming out against the shell 68.

It can now be appreciated that a brace 10 constructed according to the invention offers considerable advantages over the prior art. Of significant importance is that brace 10 is designed as a rear entry boot device without conventional laces and, thus, can be applied with ease of fitting and can be worn comfortably with a conventional shoe. The use of only two straps 30 and 46 to apply the brace 10 offers considerable convenience over prior art boot devices in applying and removing the brace 10 without tangling of boot laces with the laces of the associated shoe. Further, the elongate strap 30 and associated heel lock strap 26 extending underneath the foot and proximate to anterior talofibular ligament provides, in effect, a surrogate ligament to help minimize inversion of the ankle as well as to provide focal compression of the soft tissue in the region of the ATF ligament in the proprioceptive process. The heel lock strap 26 also serves to adjust the proper heel width when tightened and the associated elongate strap 30 also functions effectively to close the proximal portion of the brace 10 about the user's leg. Advantageously, the sleeve 42 serves to properly position the strap 30 for convenience in fitting the brace 10. The neoprene forefoot sleeve 20 and associated Lycra shin wrap 24 provide for comfort as well as anterior compression to aid in the proprioceptive process.

Figure 9:
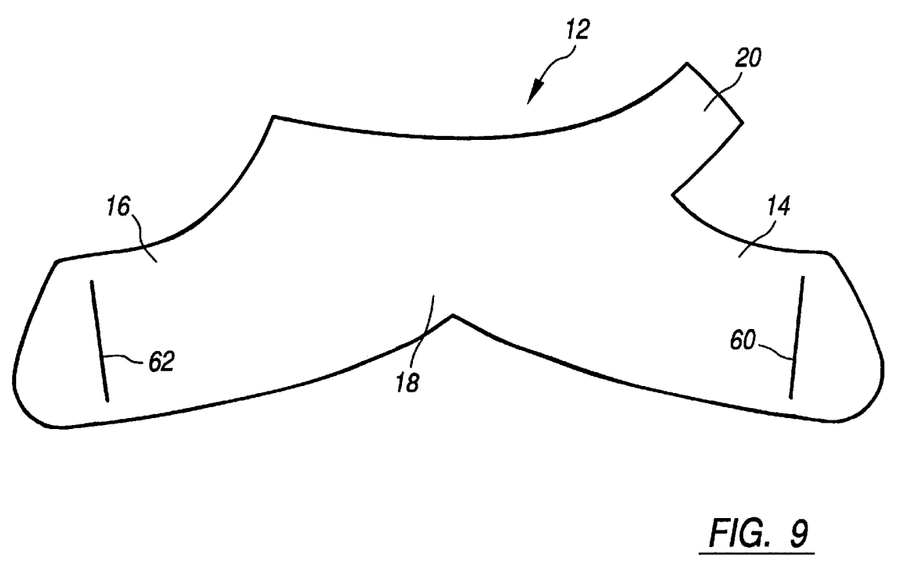
FIG. 9 is a plan view of the boot member shown in an open condition.

Referring to FIG. 9, it can also be appreciated that the boot 12 is readily constructed by die cutting a single flat piece of material, then folding the material to form the forefoot sleeve 20 with a single seam 22. Thus, the brace 10 is readily manufacturable by conventional and cost-effective methods.

While the present invention has been described in connection with preferred embodiments thereof, it will be apparent to those skilled in the art that many changes and modifications may be made without departing from the true spirit and scope of the invention. For example, while the article of the invention has been described with respect to certain fabrics and materials that are preferred for its construction, those skilled in the art will recognize that other fabrics and materials may be satisfactory. Accordingly, it is intended by the appended claims to cover all such changes and modifications as come within the spirit and scope of the invention.

What is claimed is:

1. A brace for supporting an ankle comprising:
   a unitary boot assembly constructed of flexible material and having a medial side portion dimensioned and configured to extend along a medial side of a user's leg and foot and having a lateral side portion dimensioned and configured to extend along a lateral side of said leg and foot, a forefoot sleeve portion extending from said side portions;
   a base portion connecting said side portions and said sleeve portion;
   said side portions defining a rear opening for insertion of said foot into said boot assembly; and
   relatively rigid shell members disposed in both the lateral and medial side portions of said brace, at least one of said shell members having an air cell fixed thereto.

2. The brace of claim 1 including foam material disposed internal to said air cell for preinflating said cell.

3. The brace of claim 1 including a recessed regions of said air cell to provide for anatomical conforming of said shell members to the leg and foot.

4. The brace of claim 3 including vent holes in said recessed regions.

5. The brace of claim 1 wherein said air cell comprises a proximal chamber and a distal chamber.

* * * * *